US011371012B2

(12) United States Patent
Sarks et al.

(10) Patent No.: US 11,371,012 B2
(45) Date of Patent: Jun. 28, 2022

(54) METHODS FOR PROPAGATING MICROORGANISMS FOR FERMENTATION AND RELATED METHODS AND SYSTEMS

(71) Applicant: POET Research, Inc., Sioux Falls, SD (US)

(72) Inventors: Cory James Sarks, Sioux Falls, SD (US); James Beau Schmaltz, Harrisburg, SD (US); Darren Earl Youngs, Emmetsburg, IA (US)

(73) Assignee: POET Research, Inc., Sioux Falls, SD (US)

( * ) Notice: Subject to any disclaimer, the term of this patent is extended or adjusted under 35 U.S.C. 154(b) by 15 days.

(21) Appl. No.: 16/193,485

(22) Filed: Nov. 16, 2018

(65) Prior Publication Data

US 2019/0144816 A1    May 16, 2019

Related U.S. Application Data (60) Provisional application No. 62/587,310, filed on Nov. 16, 2017.

(51) Int. Cl.
| | |
|---|---|
| *C12N 1/22* | (2006.01) |
| *C12N 1/18* | (2006.01) |
| *C12N 1/38* | (2006.01) |
| *C12P 7/06* | (2006.01) |
| *C12M 1/02* | (2006.01) |
| *C12P 7/10* | (2006.01) |

(52) U.S. Cl.
CPC .............. *C12N 1/22* (2013.01); *C12M 27/00* (2013.01); *C12N 1/18* (2013.01); *C12N 1/38* (2013.01); *C12P 7/06* (2013.01); *C12P 7/10* (2013.01); *C12P 2203/00* (2013.01)

(58) Field of Classification Search
CPC .... C12N 1/22; C12N 1/18; C12N 1/38; C12P 7/06; C12P 7/10; C12P 2203/00
See application file for complete search history.

(56) References Cited

U.S. PATENT DOCUMENTS

| | | | |
|---|---|---|---|
| 5,424,417 A | 6/1995 | Torget et al. | |
| 6,022,419 A | 2/2000 | Torget et al. | |
| 7,622,284 B2 | 11/2009 | Op Den Camp et al. | |
| 8,394,277 B2 * | 3/2013 | Bonanni | B01D 15/203 210/372 |
| 8,450,094 B1 | 5/2013 | Narendranath et al. | |
| 9,034,631 B2 | 5/2015 | Narendranath et al. | |
| 9,068,206 B1 | 6/2015 | Kwiatkowski et al. | |
| 9,234,167 B2 | 1/2016 | Narendranath et al. | |
| 9,278,379 B2 | 3/2016 | Carlson et al. | |
| 9,340,767 B2 | 5/2016 | Narendranath | |
| 9,416,376 B2 | 8/2016 | Narendranath et al. | |
| 9,469,859 B1 | 10/2016 | Bly et al. | |
| 9,540,664 B2 | 1/2017 | Lewis et al. | |
| 10,113,187 B2 | 10/2018 | Bushong et al. | |
| 10,190,086 B2 | 1/2019 | Narendranath et al. | |
| 10,435,719 B2 * | 10/2019 | Smits | C12N 1/14 |
| 2009/0098617 A1 | 4/2009 | Burke et al. | |
| 2010/0233771 A1 | 9/2010 | McDonald et al. | |
| 2014/0024826 A1 | 1/2014 | Narendranath et al. | |
| 2014/0273108 A1 | 9/2014 | Bleyer | |
| 2015/0203885 A1 | 7/2015 | Noordam | |
| 2015/0368679 A1 | 12/2015 | Narendranath et al. | |
| 2018/0171285 A1 | 6/2018 | Narendranath et al. | |
| 2018/0273988 A1 | 9/2018 | Lewis et al. | |
| 2019/0002940 A1 | 1/2019 | Karl | |
| 2019/0071696 A1 | 3/2019 | Sarks et al. | |
| 2019/0112568 A1 | 4/2019 | Narendranath et al. | |
| 2019/0185886 A1 | 6/2019 | Sarks et al. | |
| 2019/0256873 A1 | 8/2019 | Sarks et al. | |
| 2019/0292573 A1 | 9/2019 | Carlson et al. | |

FOREIGN PATENT DOCUMENTS

| | | | |
|---|---|---|---|
| CN | 101942529 A | 1/2011 | |
| WO | 2009046538 A1 | 4/2009 | |
| WO | 2011070602 A1 | 6/2011 | |
| WO | 2012103281 A2 | 8/2012 | |
| WO | 2012125739 A1 | 9/2012 | |
| WO | 2014072390 A1 | 5/2014 | |
| WO | 2014072393 A1 | 5/2014 | |
| WO | 2014072395 A1 | 5/2014 | |
| WO | 2014176531 A2 | 10/2014 | |
| WO | 2015075277 A1 | 5/2015 | |
| WO | 2015165951 A1 | 5/2015 | |
| WO | 2015165952 A1 | 11/2015 | |
| WO | 2016096971 A1 | 6/2016 | |
| WO | WO-2016120297 A1 * | 8/2016 | ................ C12P 7/10 |
| WO | 2016201031 A1 | 12/2016 | |
| WO | 2017091361 A1 | 6/2017 | |
| WO | 2017144389 A1 | 8/2017 | |
| WO | 2017201233 A1 | 11/2017 | |
| WO | 2017218380 A1 | 12/2017 | |
| WO | 2018185071 A1 | 10/2018 | |

OTHER PUBLICATIONS

U.S. Appl. No. 16/310,173; U.S. Appl. No. 16/122,401; U.S. Appl. No. 16/220,993 (Year: 2018).*
Arora et al., "Effect of Formic Acid and Furfural on the Enzymatic Hydrolysis of Cellulose Powder and Dilute Acid-Pretreated Poplar Hydrolysates", ACS Sustainable Chem. Eng. 2013, 1, 1, 23-28 (Year: 2013).*
Demeke et al., "Combining inhibitor tolerance and D-xylose fermentation in industrial *Saccharomyces cerevisiae* for efficient lignocellulose-based bioethanol production", Biotechnol Biofuels, Aug. 26, 2013;6(1):120. doi: 10.1186/1754-6834-6-120 (Year: 2013).*
Hu, S., et al., (2015) "A novel method for furfural recovery via gas stripping assisted vapor permeation by a polydimethylsiloxane membrane", Scientific Reports, 5(9428):1-9.
Zhang, K., et al., (2011) "Removal of the Fermentation Inhibitor, Furfural, Using Activated Carbon in Cellulosic-Ethanol Production", Industrial & Engineering Chemistry Research, 50:14055-14060.

(Continued)

*Primary Examiner* — Ruth A Davis
(74) *Attorney, Agent, or Firm* — Kagan Binder, PLLC (57) ABSTRACT

Disclosed are compositions, methods, and systems for propagating microorganisms for fermentation.

18 Claims, 8 Drawing Sheets

(56) References Cited

OTHER PUBLICATIONS

U.S. Appl. No. 15/778,567, filed May 23, 2018, "Using Dissolved Oxygen To Inhibit Lactic Acid Production During Propagation Of Yeast And/Or Hydrolysis Of Lignocellulosic Biomass", 22 pages.
U.S. Appl. No. 16/122,401, filed Sep. 5, 2018, "Methods And Systems For Propagation Of A Microorganism Using A Pulp Mill And/Or A Paper Mill Waste By-Product, And Related Methods And Systems", 27 pages.
Parreiras et al. (2014) "Engineering and Two-Stage Evolution of a Lignocellulosic Hydrolysate-Tolerant *Saccharomyces cerevisiae* Strain for Anaerobic Fermentation of Xylose from AFEX Pretreated Corn Stover", Plos One, 9(9):1-17.
International Search Report for International Application No. PCT/US2017/033241, dated Aug. 16, 2017, (3 pages).
Buijtenen et al., "Furfural Production by 'Acidic Steam Stripping' of Lignocellulose", ChemSusChem, pp. 2132-2136, 2013, (6 pages).
Anish et al., "Bioethanol from Lignocellulosic Biomass", Part III Hydrolysis and Fermentation, pp. 159-173, (8 pages).
Canilha et al., "Bioconversion of Sugarcane Biomass into Ethanol: An Overview about Composition, Pretreatment Methods, Detoxification of Hydrolysates, Enzymatic Saccharification, and Ethanol Fermentation", Journal of Biomedicine and Biotechnology, vol. 2012, Article ID 989572, (15 pages).

\* cited by examiner

METHODS FOR PROPAGATING MICROORGANISMS FOR FERMENTATION AND RELATED METHODS AND SYSTEMS

CROSS-REFERENCE TO RELATED APPLICATION

This application claims the benefit of priority of U.S. provisional application No. 62/587,310, filed on Nov. 16, 2017, the entire contents of which are incorporated herein by reference in its entirety.

BACKGROUND

Propagating microorganisms, namely to increase the quantity of the microorganisms, may be desirable for one or more reasons. For example, it may be desirable when the particular microorganism is expensive, for example in transporting or storing, or when the microorganism can be used as feed or feed supplements.

Also desirable is the ability to use alternative, more accessible, or more economical components in a propagation medium (e.g., lignocellulosic material, and the like). However, the hydrolysis or break down of lignocellulosic materials can produce one or more by-products that can inhibit enzymatic activity of enzymes, growth of yeast and other microorganisms, and/or fermentation of monosaccharides to a biochemical. Examples of such inhibitory compounds include acetic acid from ester hydrolysis of acetyl groups on xylan and lignin, phenolic compounds derived from lignin hydrolysis, and/or furfural and 5-hydroxymethylfurfural (HMF), which can be produced by the dehydration of pentoses and hexoses, respectively.

There is a continuing need to provide compositions, methods, and systems to reduce inhibitors such as furfural and/or to be able to use such compositions for propagating microorganisms and for fermentation.

SUMMARY

The present application provides for propagating microorganisms on lignocellulosic hydrolysates.

In one embodiment is disclosed a method of propagating a microorganism, the method comprising:
 a) providing a first propagation medium comprising at least a lignocellulosic hydrolysate comprising at least one monosaccharide at a concentration from about 0.1 wt % to 2.0 wt % of the propagation medium, and at least one inhibitor at a concentration of about 1000 ppm or less;
 b) growing a first cell mass of the microorganism on the propagation medium to form a second cell mass of the microorganism, wherein the second cell mass of microorganism is greater than the first cell mass of the microorganism; and
 c) using the second cell mass of the microorganism for fermentation to produce a fermentation product.

In another embodiment is disclosed a system for propagating a microorganism comprising:
 a) a propagation reactor vessel, wherein the propagation reactor vessel contains a propagation medium comprising at least a lignocellulosic hydrolysate; the lignocellulosic hydrolysate comprising
   i) at least one monosaccharide at a concentration from about 0.1 wt % to 2.0 wt % of the propagation medium; and
   ii) at least one inhibitor at a concentration of about 1000 ppm or less; and
 b) a first cell mass of microorganism; wherein the propagation reactor vessel is configured for growth of the first cell mass of microorganism to form a second cell mass of microorganism, wherein the second cell mass of the microorganism is greater than the first cell mass of the microorganism; and
 c) an aerator coupled to the propagation reactor vessel.

In yet another embodiment is a method of increasing fermentation rate comprising:
 a) providing a first propagation medium comprising at least a lignocellulosic hydrolysate, the lignocellulosic hydrolysate comprising:
   i) at least one monosaccharide at a concentration from about 0.1 wt % to 2.0 wt % of the propagation medium; and
   ii) at least one inhibitor at a concentration of about 1000 ppm or less propagation medium; and
 b) growing a first cell mass of the microorganism on the first propagation medium to form a second cell mass of the microorganism, wherein the second cell mass of microorganism is greater than the first cell mass of the microorganism;
 c) providing a second propagation medium comprising at least one inhibitor, a monosaccharide or both at a concentration higher than the first propagation medium;
 d) growing the second cell mass of microorganism on the second propagation medium to form a third cell mass of the microorganism; and
 e) adding the third cell mass of the microorganism with fermentable sugars to ferment the fermentable sugars to produce a fermentation product.

DETAILED DESCRIPTION

As used herein, the term "ethanologen" refers to a microorganism that can convert one or more monosaccharides (e.g., glucose and the like) into at least ethanol.

As used herein the term "lignocellulosic hydrolysate" refers to a composition that includes oligosaccharides, monosaccharides, and other products including one or more inhibitors that result from the breakdown of lignocellulosic starting materials. The hydrolysate can be broken down physically, thermally, chemically, enzymatically or combinations thereof.

As used herein the term "lignocellulosic" refers to material comprising both lignin and cellulose. Lignocellulosic material may also comprise hemicellulose.

As used herein the term "cellulosic" refers to composition comprising cellulose and additional components, including hemicellulose.

As used herein the term "saccharification" refers to the production of fermentable sugars from polysaccharides.

As used herein the term "inhibitor" refers to one or more compounds that can reduce or otherwise affect propagation, fermentation, or both. Non-limiting examples include acetic acid, furfural, 5-hydroxymethylfurfural (HMF), and combinations thereof.

As used herein the term "fermentable sugar" refers to oligosaccharides and monosaccharides that can be used by microorganism in a fermentation process.

As used herein the term "fermentation" refers broadly to the enzymatic and anaerobic breakdown of organic substances by microorganisms to produce fermentation products such as alcohols.

Figure 1:
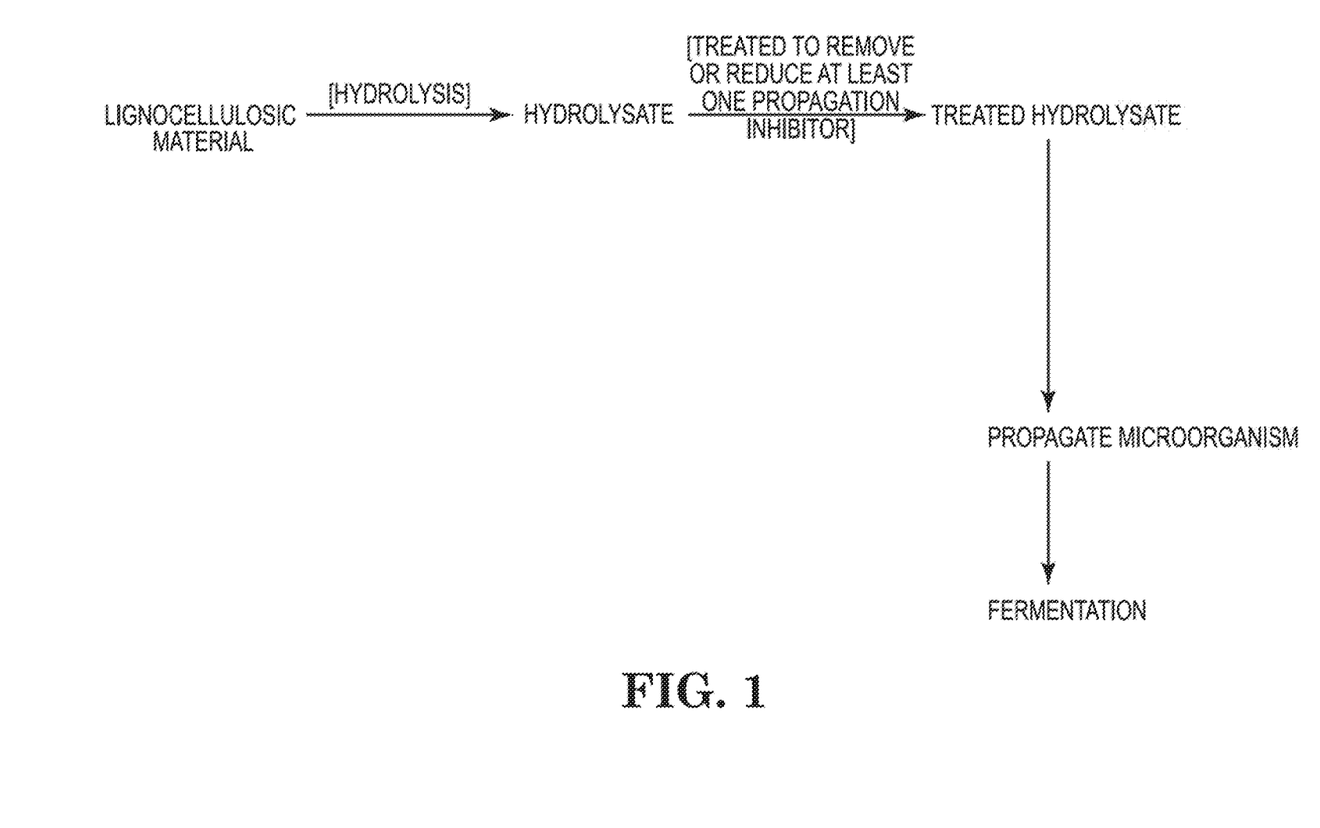
FIG. 1 shows a flow diagram of propagation and fermentation according to an embodiment.
Figure 2:
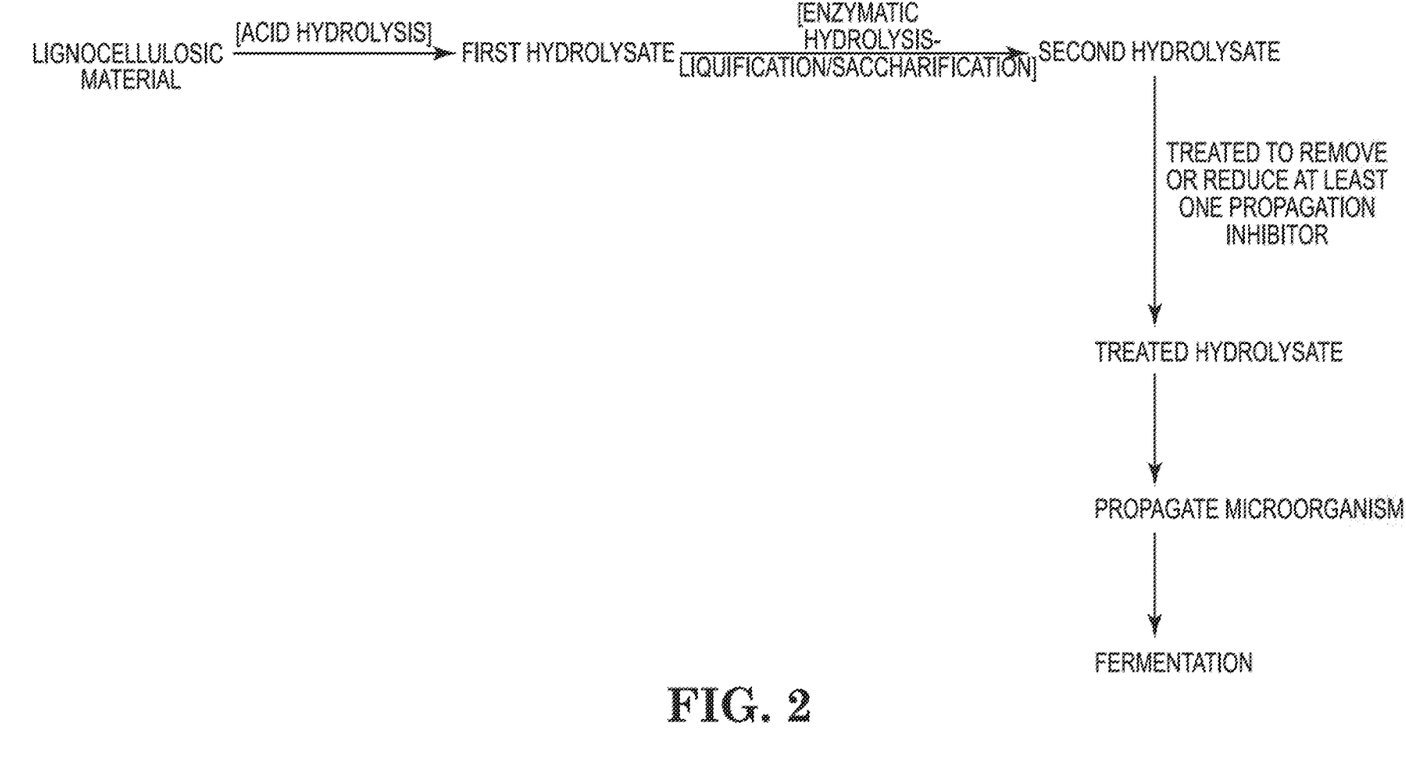
FIG. 2 shows a flow diagram of propagation and fermentation according to an embodiment.
Figure 3:
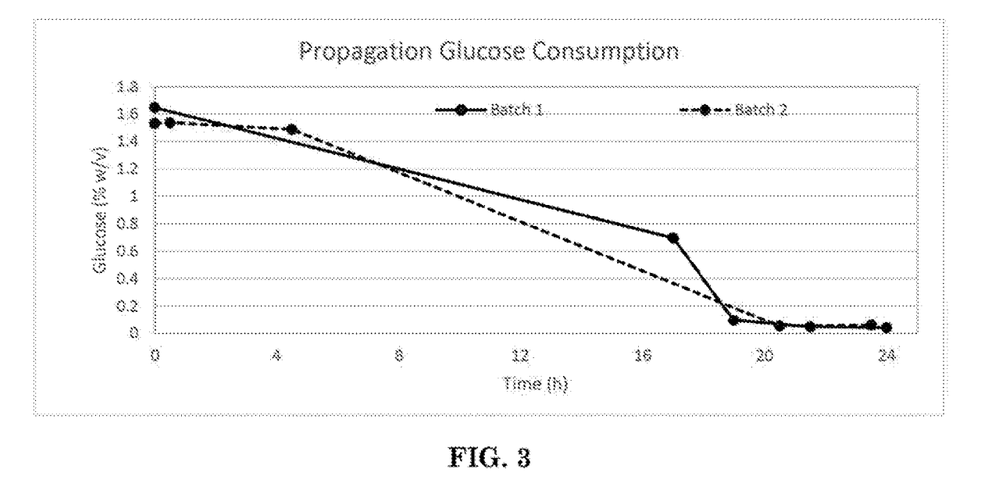
FIG. 3 is a graphical representation of glucose consumption during propagation according to an embodiment.
Figure 4:
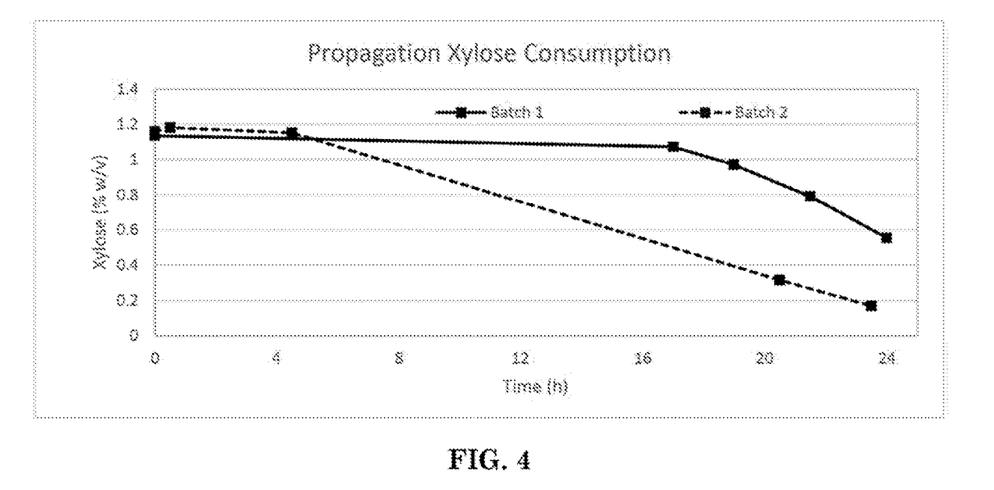
FIG. 4 is a graphical representation of xylose consumption during propagation according to an embodiment.

Disclosed are compositions, methods, and systems for propagating microorganism such as yeast. For example, propagation can be used to reproduce an initial (e.g., "starter") population of a microorganism so as to generate a larger population of the microorganism, namely increase cell numbers, that is sufficient for use in fermentation and to make a fermentation product such as alcohol. Exemplary process flow diagrams are illustrated in FIGS. 1 and 2. The disclosed compositions, methods and systems may also be used to generate or increase the amount of the microorganism population, which may be collected and dried for use as a nutritional or feed supplement or for other purposes.

As shown in FIG. 1 lignocellulosic materials are treated (e.g. by acid hydrolysis) to result in a hydrolysate. The hydrolysate is further treated to remove or reduce at least one or more inhibitors resulting in a treated hydrolysate.

In some embodiments, a portion of a hydrolysate is used for propagation whereas the remaining larger volume of the hydrolysate is used for fermentation. In some embodiments, a portion of a first or second hydrolysate as shown in FIG. 2, is used for propagation and the remaining larger volume of the first or second hydrolysate is used for fermentation. In other embodiments, the hydrolysate used for propagation is different from the hydrolysate used for fermentation.

Carbon Source

As used herein, a "carbon source" refers to one or more compounds that include at least one carbon atom and can be used by a microorganism such as yeast to grow and/or reproduce to create additional biomass. Exemplary carbon sources include monosaccharides such as glucose, fructose, galactose, mannose, xylose and the like; disaccharides such as lactose, maltose, sucrose, cellobiose and the like; oligosaccharides; polysaccharides such as cellulose, hemicelluloses, starch, xylane and the like; single carbon substrates including only one carbon atom such as methanol; and polyols such as glycerol, but not limited thereto.

In some embodiments, the carbon source comprises, consists essentially of, or consists of lignocellulosic hydrolysate. In some embodiments, the lignocellulosic hydrolysate is the entire carbon source, with no other carbon source added. In some embodiments, if a carbon source other than lignocellulosic hydrolysate is present, it is present in an amount that does not result in the Crabtree effect.

In some embodiments, a carbon source can include in addition to the lignocellulosic hydrolysate, a carbon source from fermentation processes such as stillage. In embodiments, the total carbon source in the propagation medium that may be present does not exceed 2 weight percent of the total propagation medium. Therefore, if lignocellulosic hydrolysate is able to provide a desirable carbon level, e.g. up to 2 wt % of total propagation medium, then in embodiments only lignocellulosic hydrolysate is used as the carbon source in the propagation medium. If additional carbon source is required to achieve a desirable carbon level e.g. up to 2 wt % of the total propagation medium or any other desired amount, other carbon sources may be supplied. In some embodiments, other carbon sources include stillage, thin stillage or combinations thereof. In some embodiments, if the medium needs further supplementing, additional carbon such as glucose may be added. In some embodiments, the carbon source is lignocellulosic hydrolysate. In embodiments, the carbon source present in a propagation medium ranges from 0.1 wt % to 2.0 wt % of the propagation medium, from 0.1 wt % to 1.5 wt %; from 0.2 wt % to 1.5 wt % or from 0.5 wt % to 1.5 wt %.

In some embodiments, the monosaccharide present in propagation medium ranges from 0.1 wt % to 2.0 wt % of the propagation medium, from 0.1 wt % to 1.5 wt %; from 0.2 wt % to 1.5 wt % or from 0.5 wt % to 1.5 wt %.

In some embodiments the propagation medium includes one or more inhibitors from about 1000 ppm or less, from 500 ppm or less, from 200 ppm or less. In some embodiments, the inhibitors are from 1000 ppm to 700 ppm, 750 ppm to 500 ppm, 600 ppm to 400 ppm, 500 to 200 ppm, from 500 to 150 ppm, from 300 to 100 ppm or from 200 to 1000 ppm in the propagation medium.

The yeast introduced to be propagated is initially at a range from 0.001 wt % to 0.05 wt % of the weight of the propagation medium.

In embodiments, the propagation medium includes at least one inhibitor at a concentration of about 150 ppm to 500 ppm; and at least one monosaccharide at a concentration from about 0.1% wt to 1.5 wt % of the propagation medium with yeast from about 0.001 to 0.05 wt %.

In some embodiments the yeast introduced to be propagated initially in the propagation medium includes one or more inhibitors from about 1000 ppm or less, from 500 ppm or less, from 200 ppm or less. In some embodiments, the inhibitors are from 1000 ppm to 700 ppm, 750 ppm to 500 ppm, 600 ppm to 400 ppm, 500 to 200 ppm, from 500 to 150 ppm, from 300 to 100 ppm or from 200 to 1000 ppm in the propagation medium.

Hydrolysate

In embodiments the starting material from which a lignocellulosic hydrolysate may be formed may include, for example, cellulose, lignocellulose, hemicellulose or the like. Additionally, the starting material from which the hydrolysate is obtained may be sourced from any suitable biomass or agricultural source (some nonlimiting examples of which include corn stover, corn cobs, bagasse, grasses, wood and other agricultural materials). Some nonlimiting examples of suitable hydrolysates include mixtures of different sugars, for example glucose, xylose, arabinose, cellobiose, galactose and/or fructose. In some embodiments, the hydrolysate may further include other substances such as ethanol, glycerol, furfural, hydroxymethylfurfural (HMF), one or more acids, for example one or more organic acids such as lactic acid and acetic acid and the like.

In some embodiments, the hydrolysate can be provided as part of or the entire carbon source in an amount so as to help reproduce (propagate) a desired population of a microorganism (e.g., ethanologen) within a desired amount of time.

In some embodiments, the hydrolysate can be a "whole broth" hydrolysate or a fraction thereof. As used herein a whole broth hydrolysate composition refers to a product of biomass hydrolysis and includes a solid component and a liquid component. In some embodiments, the solid component can include solid, unhydrolyzed materials of a biomass feedstock such as lignin, cellulose, and/or hemicellulose. In some embodiments, the liquid component can be a liquid hydrolysate (or liquor) and can include water, sugar and byproducts of hydrolysis such as fermentation inhibitors. Examples of fermentation inhibitors include furfural, hydroxymethylfurfural (HMF), phenol compounds, mixtures thereof, and the like. In some embodiments, a whole broth hydrolysate includes at least pentose, furfural, cellulose and/or hexose, and lignin. A whole broth hydrolysate can have a total solids (dissolved and suspended solids) content in the range from 10 to 30 percent, from 12 to 25 percent, or even from 13 to 20 percent.

How to Make a Hydrolysate Composition

Hydrolysis of polysaccharides in biomass can occur by a wide variety of techniques such as contacting the biomass with hot water, acid, base, enzyme(s), and the like.

Hydrolyzing lignocellulosic substrates to provide, e.g., xylose and/or glucose is described in, e.g., U.S. Pat. No. 5,424,417 (Torget et al.); U.S. Pat. No. 6,022,419 (Torget et al.); and U.S. Pat. No. 8,450,094 (Narendranath et al.), and U.S. Publication Number 2010/0233771 (McDonald et al.), wherein the entireties of said patent documents are incorporated herein by reference for all purposes.

Hydrolysis can create byproducts that can be inhibitory to downstream processes such as enzymatic saccharification of polysaccharide and/or oligosaccharide material and/or downstream fermentation of monosaccharides. Examples of such inhibitory byproducts from hydrolysis include acetic acid from ester hydrolysis of acetyl groups on xylan and lignin; phenolic compounds derived from lignin hydrolysis; and/or furfural and 5-hydroxymethylfurfural (HMF), which can be produced by the dehydration of pentoses and hexoses, respectively.

Before hydrolysis, a lignocellulosic feedstock can be prepared by a variety of techniques such as size reduction, steaming, combinations of these, and the like. Lignocellulosic feedstock can be prepared prior to hydrolysis such as by grinding the lignocellulosic feedstock in one or more grinders into ground solids to reduce the size of the feedstock and increase its surface area for contact with a hydrolysis medium.

Acid Hydrolysis

Acid hydrolysis can, for example, convert hemicellulose in the biomass into one or more pentoses such as xylose. In some embodiments, the acid hydrolysis includes contacting lignocellulosic biomass with an aqueous composition to hydrolyze at least a portion of the lignocellulose into one or more oligosaccharides and/or one or more pentoses, hexoses or both, and forms a first hydrolysate composition including at least pentose, cellulose, lignin, and furfural. In some embodiments, acid hydrolysis hydrolyzes at least a portion of cellulose into glucose.

During acid hydrolysis, the "severity" can be adjusted by varying one or more of time period, temperature, and pH of hydrolysis. In some embodiments, during hydrolysis an aqueous composition can have a pH in the range from 1 to 5, or even 2 to 3. The aqueous composition can include an acid such as sulfuric acid present in a concentration in the range from 0.2 to 1.3% w/w, or even 0.5 to 1% w/w. In some embodiments, acid hydrolysis can be performed for a time period in a range from 15 minutes to 5 hours, or even 30 minutes to 4 hours. In some embodiments, acid hydrolysis can be performed at a temperature in the range from greater than 100° C. to 170° C., or even from 110° C. to 150° C.

Acid hydrolysis can be performed in a variety of system and apparatus configurations. In some embodiments, an acid hydrolysis system can include a first reactor system in fluid communication with a source of lignocellulosic biomass and a source of an aqueous composition. The first reactor system can include at least one reactor configured to contact the lignocellulosic biomass with the aqueous composition to hydrolyze at least a portion of the hemicellulose into one or more oligosaccharides and/or one or more pentoses, and form a first hydrolysate composition including at least pentose, cellulose, lignin, and furfural.

Optional Steam Explosion

Optionally, the first hydrolysate from acid hydrolysis can be subjected to steam explosion conditions that make the cellulose in the first hydrolysate more accessible during enzymatic hydrolysis. In some embodiments, steam explosion also forms furfural. Steam explosion can be performed in a system that includes at least one reactor configured to receive the hydrolysate and subject the cellulose in the hydrolysate to a steam explosion process under conditions that form a steam-exploded, hydrolysate composition including at least cellulose, lignin, and furfural.

During steam explosion, cellulose (either in a hydrolysate or hydrolysate with a portion of xylose liquor removed) can be subjected to a relatively elevated pressure and temperature so that moisture impregnated within the cellulose network is in a liquid state. Then, the pressure can be reduced so that the liquid "flashes" to a gas state so that the sudden expansion with the cellulose network causes at least a portion of the cellulose structure to rupture, thereby increasing the surface area of the cellulose for increased exposure to cellulase enzymes. In some embodiments, the superheated hydrolysate composition can be flashed to a reduced pressure by continuously discharging the composition through an orifice. In some embodiments, a hydrolysate composition including cellulose can be subjected to a temperature in the range from 320° F. to 400° F. and a pressure in the range from 75 psig to 235 psig, followed by suddenly exposing the hydrolysate composition to a reducing pressure such as atmospheric pressure. In some embodiments, a hydrolysate composition including cellulose can be subjected to a temperature in the range from 350° F. to 385° F. and a pressure in the range from 120 psig to 195 psig, followed by suddenly exposing the hydrolysate composition to a reducing pressure such as atmospheric pressure.

Depending on the amount of inhibitors present in the carbon source or other sources, inhibitor such as furfural or HMF can be stripped from the steam-exploded hydrolysate using a stripping device to inject a gas into the hydrolysate and recover a gas that includes at least a portion of the stripped inhibitor.

In embodiments, after steam explosion, an inhibitor such as furfural can be stripped from the steam-exploded hydrolysate using a furfural stripping device to inject a gas into the hydrolysate and recover a gas that includes at least a portion of the stripped furfural. Gas stripping of an inhibitor such as furfural is further discussed in PCT International Application Publication No. WO 2017/201233, which entire application is incorporated herein by reference.

In embodiments, first hydrolysate from acid hydrolysis can be separated prior to steam explosion into a xylose liquor stream and a solid component stream including at least cellulose and lignin. The xylose liquor can be separated from the solid component after hydrolysis via one or more of centrifugation, filtering, and the like. The solid component stream can be subjected to steam explosion conditions to make the cellulose in the solid component stream more accessible during enzymatic hydrolysis. Advantageously, by separating at least a portion of the xylose from the cellulose into a liquor stream, the xylose in the liquor stream can avoid steam explosion condition so that such xylose is not converted to furfural. Nonetheless, steam explosion of the cellulose in the solid component stream can still create furfural due a residual amount of xylose that may remain in solid component stream.

In an embodiment, steam explosion can be performed in a steam explosion system that is in fluid communication with a separation system (not shown). The separation system can be coupled to the acid hydrolysis system to separate the first hydrolysate into the xylose liquor stream and the solid component stream. After steam explosion, the solid component stream and the xylose liquor stream can be recombined and subjected to enzymatic hydrolysis.

Enzymatic Hydrolysis

After acid hydrolysis and optional steam explosion, at least a portion of the cellulose in the hydrolysate composition can be enzymatically hydrolyzed to hydrolyze the cellulose into glucose. In some embodiments, at least a portion of the cellulose in the first hydrolysate composition provided directly from acid hydrolysis can be enzymatically hydrolyzed to form a second hydrolysate composition that includes at least pentose (e.g. xylose), hexose (e.g. glucose), lignin, and furfural.

In some embodiments, enzymatic hydrolysis can include liquefying (liquefaction) at least a portion of the cellulose in the hydrolysate followed by saccharifying (saccharification) at least a portion of the liquefied cellulose to form glucose. Liquefaction can include adding one or more cellulase enzymes to the hydrolysate composition to liquefy at least a portion of the cellulose.

A liquefaction system can include one or more vessels (not shown) containing a hydrolysate and configured to maintain the hydrolysate at a pH and temperature for a time period to convert at least a portion of the cellulose in the lignocellulosic biomass into an oligosaccharide and/or a monosaccharide. In some embodiments, the temperature of the hydrolysate during at least a portion of liquefaction is in a range from 45° C. to 65° C., or even from 50° C. to 60° C. In some embodiments, the pH of the hydrolysate during at least a portion of liquefaction is in a range from 4 to 6, or even from 4.5 to 5.5. In some embodiments, the liquefaction time period is in the range from 2 to 20 hours, or even from 6 to 8 hours.

Saccharification is in fluid communication with the liquefaction system. In some embodiments, a saccharification system can include at least one reactor configured to receive the liquefied cellulose so as to saccharify at least a portion of the liquefied cellulose and form glucose. A saccharification system can include one or more batch reactors (not shown) in fluid communication with the liquefaction system 225 to receive the liquefied cellulose. The saccharification system can be configured to maintain a hydrolysate at a pH and a temperature for a time period to convert at least a portion of the cellulose in the lignocellulosic biomass into an oligosaccharide and/or a monosaccharide. In some embodiments, the temperature of the hydrolysate can be in a range from 45° C. to 65° C., or even from 50° C. to 60° C. In some embodiments, the pH of the hydrolysate can be in a range from 4 to 6, or even from 4.5 to 5.5. In some embodiments, the saccharification time period is in the range from 48 to 120 hours, or even from 112 to 114 hours.

In addition to a carbon source, a non-carbon source or nutrient source may also be included to help propagate microorganisms such as ethanologens. As used herein, a "non-carbon source" refers to one or more materials or nutrients that can be used by a microorganism to grow and/or reproduce to create additional microorganisms and is different from a carbon source. In embodiments, the non-carbon source or nutrients can be used as a carbon source.

In embodiments, the propagation media can include non-carbon sources or nutrients. In embodiments a stillage component (e.g. whole stillage, thin stillage and/or syrup) may be added to the propagation medium. In embodiments, stillage provides a nutrient source in the propagation medium.

Whole stillage is well-known and is a byproduct of distilling a fermentation product. For example, a well-known process for making whole stillage is a corn grain-to-ethanol process. Grain such as corn, barley, wheat, and/or sorghum is prepared in system so that it can be fermented into a fermentation product that includes one or more biochemical such as ethanol. Either the whole grain can be used or only one or more portions of the grain can be used. For example, whole grains for fermentation are milled or fractionated into one or more separated portions before milling. After milling, the milled grain material can be further processed to break down polysaccharides and/or oligosaccharides into one or more monosaccharides such as glucose that can be fermented by, e.g., yeast. Methods of breaking down polysaccharides such as starch into glucose are well known and include e.g. hot water, such as hot water that includes an added acid such as sulfuric acid, and/or enzymatic pretreatment or simultaneous saccharification and fermentation. After fermentation, the fermentation product is distilled in a system, where the ethanol is removed from the fermented mash in a distillation column. After the ethanol is removed, the remaining residue is removed as stillage residue. The stillage residue is known as "whole stillage." The whole stillage can be optionally further processed via one or more systems to further clarify or separate the whole stillage before being delivered to propagation system. For example, the whole stillage can be subjected to a solid-liquid separation process to produce a solid stream of residue, also known as wet cake, and a liquid stream of residue, also referred to as thin stillage. The thin stillage can be further processed to increase the solids concentration by evaporation resulting in condensed distillers solubles or syrup. Typically the syrup is mixed back with the separated solid stream or wet cake and fed to a dryer to remove the remaining moisture. The resulting dry solids are referred to as Dried Distillers Grains and Solubles or "DDGS", and can be sold as animal feed.

Such stillage component from the grain-to-ethanol producing process, including the whole stillage, wet cake, thin stillage, and/or syrup can be used as at least part of the non-carbon source for propagating microorganisms such as yeast. Using at least a portion of the whole stillage provides an alternative or additional non-carbon source as compared to, e.g., yeast extract. Using whole stillage or thin stillage as the entire amount of nutrients or part of the nutrients can propagate yeast as well as, or better than, other non-carbon sources such as yeast extract.

In some embodiments, the non-carbon source includes a stillage component such as thin stillage, wetcake, syrup, and any combination thereof. The non-carbon source can include syrup derived from thin stillage, thin stillage, or combinations thereof. In some embodiments, the nutrient source can include known nitrogen sources such as yeast extract and urea.

The stillage component can be provided in any amount so as to help reproduce (propagate) and generate a desired population of microorganism (e.g., ethanologen) within a given amount of time. The amount of stillage component provided can depend on factors such as the type and amount of other non-carbon sources present, the type and amount of carbon sources present, pH, temperature, desired time period for propagation, and the like. In some embodiments, the non-carbon source is provided only as a stillage component such as thin stillage.

In some embodiments, stillage is added to the propagation medium at around 10-35 wt % of the propagation medium. In other embodiments, the stillage is added at about 20-30 wt % the propagation medium. In some embodiments, the stillage component (e.g. thin stillage) contains less than 5000 mg/L of acetic acid, less than 8000 mg/L of lactic acid or both. In some embodiments, the non-carbon source includes thin stillage but no yeast extract, urea or both. In some embodiments, additional nutrients are supplied in addition to stillage. In some embodiments, the non-carbon source includes yeast extract, urea or both.

Propagating a microorganism that can convert one or more monosaccharides into a biochemical will be described below by reference to an ethanologen such as genetically modified yeast for making ethanol. The present disclosure, however, is not limited to propagating only such yeast and it should be understood that propagating any other microorganism (e.g. genetically modified or non-genetically modified) is contemplated.

Propagating a microorganism (e.g. an ethanologen includes combining a first cell mass of the microorganism with at least a hydrolysate composition to facilitate growth of a sufficient amount of ethanologen (i.e. ethanologen second cell mass) for inoculation (i.e. ethanologen inoculum to be supplied) to a fermentation system. The first cell mass of the microorganism (e.g., ethanologen) can be included either while the medium is being formed, after the medium is formed, or both.

According to an exemplary embodiment the propagation medium for the propagation system includes a carbon source including hydrolysate, a non-carbon source having stillage as all or part of the non-carbon source, and, optionally, one or more additional agents (not shown).

Optional additional agents for propagating yeast are well known and include, e.g., agents supplied with an ethanologen such as antibiotics, supplemental or accessory enzymes, materials for adjusting and maintaining pH, nutrients or other components providing nutritional or other benefits to the microorganism. Optional additional nutrients include, e.g., yeast extract, urea, diammonium phosphate, magnesium sulfate, zinc sulfate or other salts, and the like.

The ratio of non-carbon source to carbon source is selected to grow a desired cell mass of microorganism such as a sufficient size cell mass of yeast for fermentation in a cellulosic ethanol process. Factors in selecting the ratio of non-carbon source to carbon source include the type(s) and amount(s) of non-carbon sources, the type(s) and amount(s) of carbon sources, types and amounts of additional propagation medium agent(s), the types and initial amounts of microorganisms, the time period targeted for growing the microorganism, pH, temperature, and the like. Additional considerations include whether it is desired to condition the microorganisms during propagation to the environment expected during fermentation. Conditioning microorganisms to the fermentation environment can advantageously help the microorganisms operate (e.g., convert sugar to ethanol) more effectively.

Propagating the microorganism can begin when the microorganism is present in the propagation medium and desired conditions are present. Conditions to consider for propagation of a microorganism include, e.g., amount of ingredients, pH, time period for growth of the microorganism, stir speed (if stirring is present), exposure to oxygen, temperature, and the like.

In some embodiments, the first cell mass (e.g., initial cell mass) of the microorganism is present in an amount less than 5 grams of ethanologens per liter of medium, less than 2 grams of ethanologens per liter of medium, or less than 0.5 grams of microorganism per liter of medium. In some embodiments, the first cell mass of the microorganism is from 0.5 to 1 grams of microorganism per liter of medium. In some embodiments, the first cell mass of the microorganism is from 0.05 to 2 grams of microorganism per liter of medium, 0.05-0.5 grams of microorganism per liter of medium.

The cell mass can be propagated, depending on conditions, for a time to produce a desired cell mass. Typically, the desired cell mass is a size sufficient to ferment sugar into an alcohol (e.g., ethanol) within an economically desirable time period. Exemplary time periods include from 12-80 hours, 24-48 or 48-80 hours. In exemplary embodiments, the desired (e.g., second or final) cell mass of the microorganism (e.g. yeast) is present in an amount in the range from 10 to 1000 times the initial or first cell mass of the microorganisms, 200-1000 times, 300 to 800, 500-1000 times; 100-1000 times; 10 to 30 times the initial or first cell mass of the microorganisms, from 20-30 times or 15 to 25 times, or from 15 to 35 times the initial or first cell mass of the microorganisms. In embodiments the second cell mass of the organism is grown within a time period in the range of from 8 to 80, from 12-48 hours, from 12-24 hours or from 12 to 60 hours, wherein the time period begins when the first cell mass of the microorganism is combined with the carbon source to propagate the first cell mass of the microorganism.

The pH of the propagation medium can be at a pH that helps reproduce (propagate) and generate a desired population of microorganism (e.g., ethanologen) within a desired amount of time. In some embodiments, the pH is between 4 and 8, between 5 and 7, or between 4.5 and 6. Techniques for adjusting and maintaining pH of a propagation medium for propagating microorganisms such as an ethanologen are well known and include, e.g., adding one or more acidic materials and/or adding one or more basic materials.

The temperature of the propagation medium can be at a temperature that helps reproduce (propagate) and generate a desired population of microorganism (e.g., ethanologen) within a desired amount of time. In some embodiments, the temperature is at a temperature in the range of from 15° C. to 50° C., from 20° C. to 40° C., or from 25° C. to 40° C. or 20-37° C.

In some embodiments the second or final cell mass of the microorganism is present in an amount in the range of from 10-30 times the initial or first cell mass within a time period in the range of from 12 to 48 hours, at a pH from about 4-6 and at a temperature from 20-30° C.

Propagation of a microorganism can be performed according to a continuous process, fed-batch process, a batch process, or combinations thereof. Preferably, batch process has certain benefits associated therewith. A batch process can be highly desirable as it can be relatively easier to manage and control as compared to a continuous or fed-batch process.

In some embodiments, the propagation medium is stirred, or oxygen is otherwise added, for at least a portion of the propagation process so as to provide sufficient oxygen levels throughout the medium so as to promote aerobic respiration and, therefore, reproduction of the microorganism instead of, e.g., anaerobic fermentation production of ethanol. In some embodiments, if sufficient oxygen is not provided to the propagation medium, the process can switch to an anaerobic pathway and promote fermentation so as to produce alcohol to an undue degree.

Also disclosed is a propagation system in which in embodiments, propagation is performed in one or more stages. For example, where yeast is the microorganism to be propagated, the propagation system can include at least two stages. In a first stage, a yeast culture can be grown into an initial yeast inoculum. In the first propagation stage, the initial yeast inoculum is introduced into a vessel and diluted (e.g. by 250×). In the vessel, the initial yeast inoculum and a portion of the carbon source (e.g., treated hydrolysate), a portion of the non-carbon source (e.g., thin stillage), and water may be supplied along with optional additional agents (discussed above). According to exemplary embodiments, the temperature may be maintained in a range of about 26 to 37 degrees Celsius and the pH in a range of about 3.5 to 6.5 for a time of at least 24 hours. For example, yeast can be grown in the first propagation stage under conditions including a temperature of about 30 degrees Celsius and a pH of about 5.5 for about 24 hours.

In the second propagation stage, the yeast inoculum from the first propagation stage is diluted (e.g. by 10×), typically after being transferred to another vessel. In the vessel, the yeast inoculum from the first propagation stage and a portion of the carbon source, a portion of the non-carbon source, and water may be supplied along with optional additional agents (discussed above). According to exemplary embodiments, the temperature may be maintained in a range of about 26 to 37 degrees Celsius and the pH in a range of about 3.5 to 6.5 for a time of at least 24 hours. For example, yeast can be grown in the second propagation stage under conditions comprising a temperature of about 30 Celsius and a pH of about 4.5 to about 5.5 for about 24 hours.

According to an embodiment, the yeast cell mass will grow by about 200 to 500 fold in the first stage and about 20 to 40 fold in the second stage.

After propagation, cell mass of microorganism is provided to a fermentation system so as to ferment a biomass such as pretreated lignocellulosic material and produce ethanol.

In some embodiments, the yeast propagated on treated hydrolysate after a period of time is further grown or propagated on hydrolysate, namely hydrolysate that is not stripped of inhibitors such as furfural and the like. The un-treated hydrolysate or hydrolysate is added to the propagation vessel for an additional one to 3 hours under conditions used to propagate the microorganisms. Without being bound by any theory, this exposure of already-propagated microorganism to hydrolysate that is not further stripped of inhibitors "adapts" or "conditions" the micrograms before exposing the microorganism to fermentation conditions.

In some embodiments, microorganisms (e.g. yeast) that have been propagated from an initial or first cell mass of microorganism to a second cell mass of microorganisms can be further grown for an additional time period to produce a third cell mass of microorganisms. In embodiments, the second cell mass of microorganisms are grown on a hydrolysate composition comprising inhibitors from about 500 ppm to 4200 ppm, from 600 ppm to 4000 ppm, 500 to 3500 ppm. In embodiments the inhibitors include furfural at 500 ppm to 4200 ppm, from 600 ppm to 4000 ppm, 500 to 3500 ppm. In embodiments, the second cell mass of microorganisms are "conditioned" after a period of propagation for about 1 to 3 hours, from 1-2 hours or 2-3 hours at 20-30° C. and at a pH from 5 to 6.

In some embodiments, the first cell mass of the microorganism is from 0.01 to 1 grams of microorganism per liter of medium that is propagated on a lignocellulosic hydrolysate that includes 2000 ppm or less of inhibitor and at least one monosaccharide at a concentration from 0.1 wt % to 2 wt % of the hydrolysate. The first cell mass is grown for 12-72 hours and a pH from 4-7 to result in the second cell mass of the microorganism which is in the range of 5 to 500 times the initial or first cell mass of the microorganism.

The resultant microorganisms that are propagated by the described methods are used to convert, namely ferment, a carbon source to a desired bio product. In embodiments, the microorganisms are grown on fermentable sugars to convert sugar into ethanol. The microorganisms used for fermentation are microorganisms that have been propagated by the methods described herein or by microorganisms that are further "conditioned."

When microorganisms are exposed to inhibitors greater than the inhibitor concentrations present at propagation, such microorganisms are found to result in an increase in fermentation. In some embodiments, the increase in fermentation is an increase in the consumption of fermentable sugars. In embodiments, microorganisms that are exposed to greater sugar, inhibitors, or both showed better fermentation rates compared to microorganisms propagated as fed-batch with around 1 to 2 wt % monosaccharides and around 100-300 ppm inhibitors medium.

Microorganisms

Microorganisms that can convert one or more monosaccharides into a biochemical or fermentation product are well known and include, e.g., bacteria and/or fungi such as yeast. The biochemical can vary depending on the conditions that are provided. In many embodiments, the biochemical includes biofuels such as ethanol, butanol, and the like. In some embodiments, the microorganism includes one or more ethanologenic microorganisms referred to as "ethanologens".

The microorganism to be propagated and later used for fermentation include prokaryotic (e.g. bacteria) and eukaryotic (e.g. yeast, fungi and algae) microorganisms. Exemplary bacterial microorganisms include the genera *Escherichia, Bacillus, Klebsiella, Lactobacillus, Lactococcus*, and the like. Exemplary algae include the genus *Chlorella, Thraustochytriu, Schizochytrium, Crypthecodinium*, and the like. In some embodiments, the algae are heterotrophic algae.

Exemplary yeast and fungus include the genus of, *Aspergillus, Candida, Pichia*, (*Hansenula*), *Phanerochaete*,

*Kloeckera (Hanseniaspora), Kluyveromyces, Rhodotorula, Torulopsis, Zygosaccharomyces, Yarrowia,* and *Saccharomyces*.

In some embodiments, the microorganisms include *Escherichia coli, Klebsiella oxytoca, Zymomonas mobilis, Clostridium thermocellum, Pichia pastoris, Pichia stipites, Candida albicans, Saccharomyces cerevisiae, Phanerochaete chrysosporium Schizosaccharomyces pombe,* and/or *Yarrowia lipolytica.*

In some embodiments, the microorganism to be propagated includes genetically modified yeast such as genetically modified *Saccharomyces cerevisiae*. According to one embodiment, the yeast is a strain of *Saccharomyces cerevisiae* yeast. In some embodiments, the yeast is a strain of *Saccharomyces cerevisiae* capable of converting, namely fermenting, glucose, xylose, arabinose or a combination thereof. In some embodiments, the yeast is a genetically modified strain of *Saccharomyces cerevisiae* yeast capable of growing on hydrolysate or treated hydrolysate. In still other embodiments, the yeast strain is a non-genetically modified strain (e.g. *Saccharomyces cerevisiae*).

Suitable yeasts include any of a variety of commercially available yeasts, such as commercial strains of *Saccharomyces cerevisiae* available under the trade names, e.g., Ethanol Red® from LeSaffre or TransFerm® from Mascoma Corporation. Exemplary yeast strains can ferment xylose and/or glucose into an alcohol such as ethanol. For example, a useful strain of yeast includes *Saccharomyces cerevisiae* yeast altered to convert (i.e., ferment) xylose and glucose to ethanol (i.e., a genetically modified yeast derived from an organism as described in U.S. Pat. No. 7,622,284). As another example, a useful strain of yeast includes *Saccharomyces cerevisiae* yeast altered (i.e., genetically modified) to convert (i.e., ferment) xylose, arabinose, and glucose to ethanol.

Additional embodiments include the following:
1. A method of propagating a microorganism, the method comprising:
   a) providing a first propagation medium comprising a carbon source component, the carbon source component comprises at least a lignocellulosic hydrolysate comprising at least one monosaccharide and at least one inhibitor at a concentration of about 1000 ppm or less, wherein the at least one monosaccharide is at a concentration from about 0.1 wt % to 2.0 wt % of the propagation medium; and
   b) growing a first cell mass of the microorganism on the propagation medium to form a second cell mass of the microorganism, wherein the second cell mass of microorganism greater than the first cell mass of the microorganism.
2. The method as in embodiment 1, wherein the first cell mass of the microorganism is from about 0.001 wt % to 0.05 wt % of propagation medium.
3. The method as in any one of the preceding embodiments, wherein the at least one inhibitor comprises furfural, 5-hydroxymethylfurfural (HMF) or combinations thereof.
4. The method as in any one of the preceding embodiments, wherein providing the carbon source comprises:
   a) forming a lignocellulosic hydrolysate composition comprising at least one inhibitor greater than 1000 ppm; and
   b) reducing the at least one inhibitor to less than 1000 ppm.
5. The method as in embodiment 4, wherein the reducing is by dilution or gas stripping or both.
6. The method as in any one of embodiments 4-5, wherein the gas stripping is by with air, nitrogen, ozone or combinations thereof.
7. The method as in any one of the preceding embodiments, wherein the second cell mass of the microorganism comprises 100 to 1000 times the first cell mass of microorganisms.
8. The method as in any one of the preceding embodiments, wherein the second cell mass of the microorganism comprises 10-30 times the cell mass of microorganisms.
9. The method as in any one of the preceding embodiments, wherein the propagation medium further comprises a non-carbon source.
10. The method as in any one of the preceding embodiments, wherein the non-carbon source comprises a by-product of fermenting a grain material.
11. The method as in any one of the preceding embodiments, wherein the by-product of fermenting a grain material comprises stillage component.
12. The method as in any one of the preceding embodiments, wherein the stillage component is thin stillage.
13. The method as in any one of the preceding embodiments, wherein substantially no ethanol is produced by the first cell mass of the microorganism or second cell mass of the microorganism during the growing time period.
14. The method as in any one of the preceding embodiments, wherein the second cell mass of the ethanologens is present in an amount in the range of from 10 times to 30 times the first cell mass within a time period from 12 hours to 48 hours, wherein the time period begins when the first cell mass of the ethanologens is combined with the propagation medium to propagate the first cell mass of the ethanologens grown at about 20° C. to 37° C. at pH from about 4 to 6.
15. The method as in any one of the preceding embodiments, wherein the method further comprises growing the second cell mass of microorganism on a carbon source having an inhibitor concentration, or monosaccharide concentration or both greater than the first carbon source to form a third cell mass of the microorganism.
16. The method as in any one of the preceding embodiments, wherein the microorganism comprises yeast.
17. The method as in any one of the preceding embodiments, wherein the yeast comprises genetically modified yeast.
18. The method as in any one of the preceding embodiments, wherein the yeast is *Saccharomyces cerevisiae.*
19. The method as in any one of the preceding embodiments, wherein the yeast is capable of growing on glucose, xylose, arabinose or a combination thereof.
20. The method as in any one of the preceding embodiments further comprising using the second cell mass of the microorganism or the third cell mass of microorganism or combinations thereof to ferment a fermentable sugar to produce a fermentation product.
21. The method as in any one of the preceding embodiments, wherein the fermentation product is ethanol.
22. A system for propagating a microorganism comprising:
   (a) a propagation reactor vessel, wherein the propagation reactor vessel contains a propagation medium comprising a carbon source, the carbon source comprising:
      i) at least a lignocellulosic hydrolysate;
      ii) at least one monosaccharide at a concentration from about 0.1 wt % to 2.0 wt % of the propagation medium; and iii) at least one inhibitor at a concentration of about 1000 ppm or less; and (b) a first cell mass of microorganism; wherein the propagation reactor vessel is configured for growth of the first cell mass of microorganism to form a second cell mass of microorganism, wherein the second cell mass of the microorganism is greater than the first cell mass of the microorganism; and (c) an aerator coupled to the propagation reactor vessel.

23. A method of increasing fermentation rate comprising:
a) providing a propagation medium comprising a first carbon source, the first carbon source comprising;
   i) at least a lignocellulosic hydrolysate;
   ii) at least one monosaccharide at a concentration from about 0.1 wt % to 2.0 wt % of the propagation medium; and
   iii) at least one inhibitor at a concentration of about 1000 ppm or less propagation medium; and
b) growing a first cell mass of the microorganism on the propagation medium to form a second cell mass of the microorganism, wherein the second cell mass of microorganism is greater than the first cell mass of the microorganism;
c) providing a second carbon source comprising at least one inhibitor, a monosaccharide or both at a concentration higher than the first carbon source;
d) growing the second cell mass of microorganism on the second carbon source to form a third cell mass of the microorganism; and
e) adding the third cell mass of the microorganism with fermentable sugars to ferment the fermentable sugars to produce a fermentation product.

24. The method as in embodiment 23, wherein the fermentation rate is greater using the third cell mass compared to the second cell mass of microorganisms.

Example 1 (Presence of Inhibitors)

Slurries (referred as propagation slurry Batch 1 and Batch 2) were obtained from a commercial lignocellulosic ethanol facility. Each slurry contained acid pretreated and enzymatically hydrolyzed corn stover that were used for propagation.

Batch 1 propagation slurry contained about 724 ppm furfural, 50 ppm 5-hydroxymethylfurfural (HMF), 0.38% w/v acetic acid, 1.65% w/v glucose, and 1.14% w/v xylose.

Batch 2 contained about 68 ppm furfural, 28 ppm HMF, 0.42% w/v acetic acid, 1.53% w/v glucose, and 1.16% w/v xylose.

To each batch was added grain ethanol thin stillage, and water. The propagation slurries were each added to 70% volume of the 6.6 L Bioflo 310 bioreactor. The bioreactor was aerated and controlled at 31.1° C. and pH 5.5. Créme yeast from Novozymes was added at approximately 0.2 g/L DCW. The propagation was allowed to continue until dissolved oxygen and near infrared testing showed that sugar had been consumed by the yeast (>50% xylose consumption).

Once propagation was complete, 10% by volume of the propagation slurry was combined with 90% by volume of the similar acid pretreated and enzymatically hydrolyzed corn stover that was previously pH adjusted to 5.5 in a shake flask topped with a water lock to provide the fermentation slurries. The fermentation slurries were allowed to ferment for 72 hours at 32° C. in an air shaker incubator.

Fermentation slurries referred to as fermentation slurry Batch I and Batch II were each used for fermentation.

Fermentation slurry Batch 1 contained about 891 ppm furfural, 54 ppm HMF, 0.39% w/v acetic acid, 2.6% w/v glucose, and 1.68% w/v xylose.

Fermentation slurry Batch 2 contained about 1111 ppm furfural, HMF was below the detection limit, 0.45% w/v acetic acid, 3.5% w/v glucose, and 2.2% w/v xylose.

Figure 5:
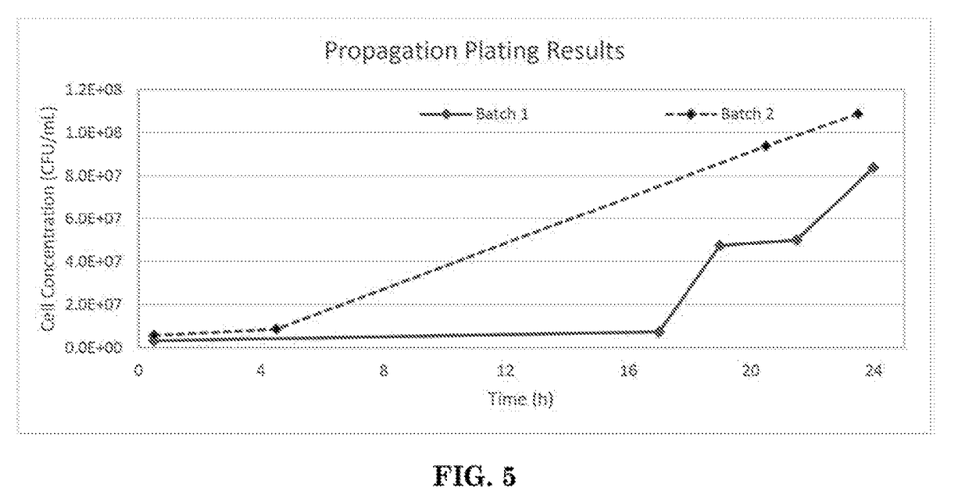
FIG. 5 is a graphical representation of propagation as determined by plating according to an embodiment.
Figure 6:
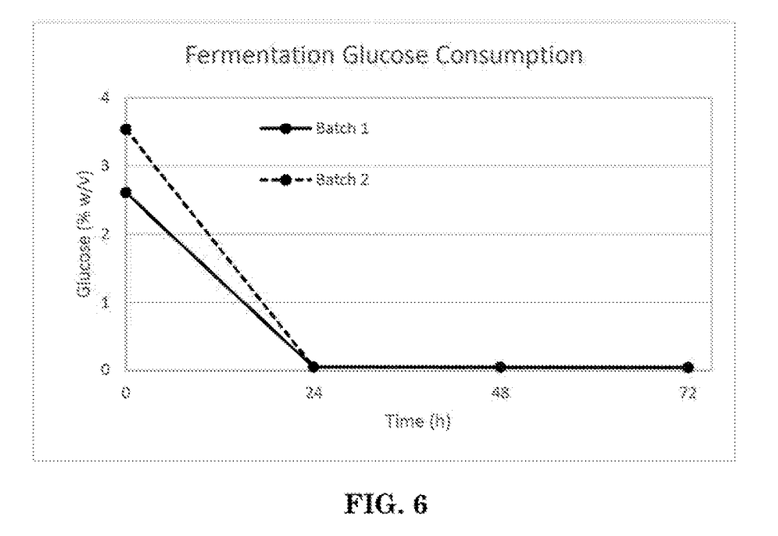
FIG. 6 is a graphical representation of glucose consumption during fermentation according to an embodiment.
Figure 7:
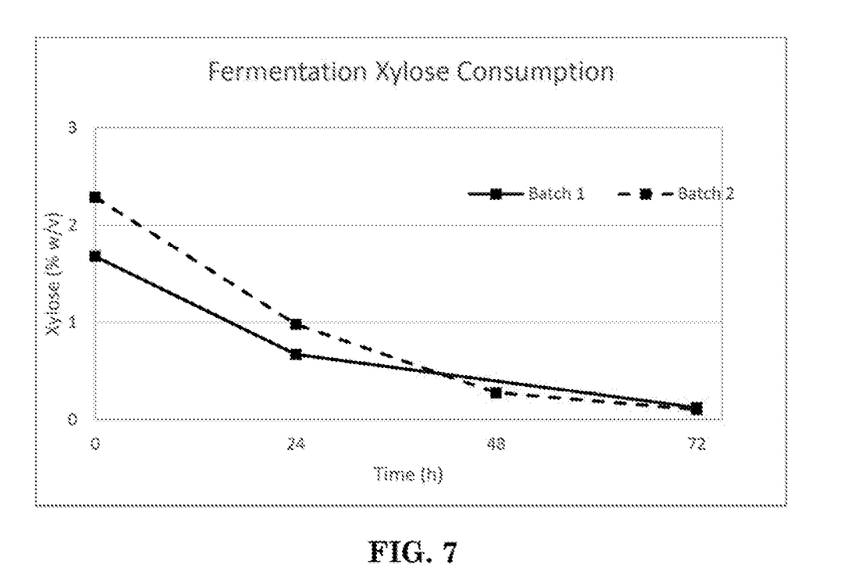
FIG. 7 is a graphical representation of xylose consumption during fermentation according to an embodiment.
Figure 8:
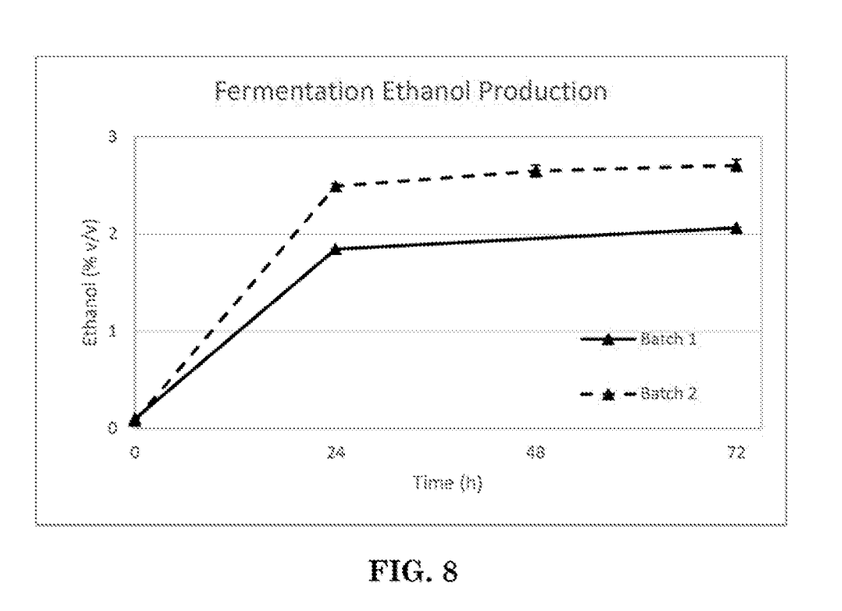
FIG. 8 is a graphical representation of ethanol production during fermentation according to an embodiment.
Figure 9:
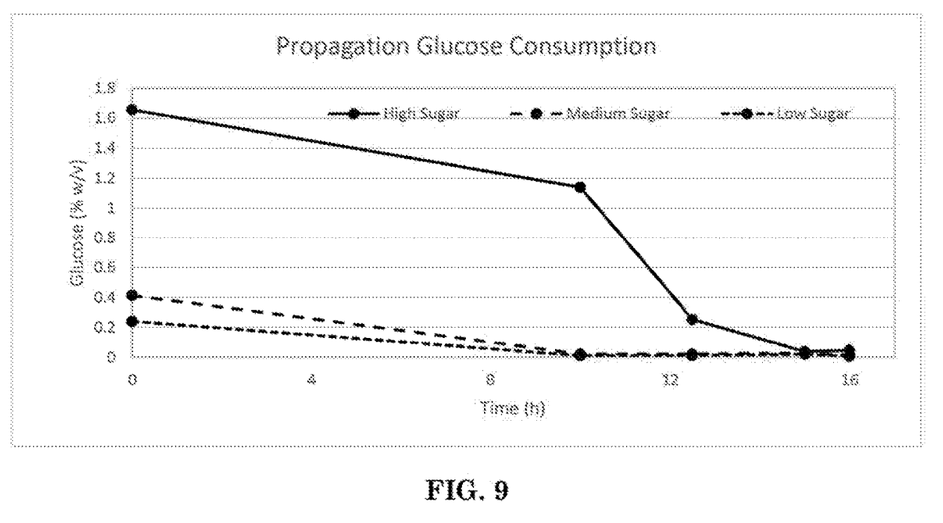
FIG. 9 is a graphical representation of glucose consumption during propagation according to an embodiment.
Figure 10:
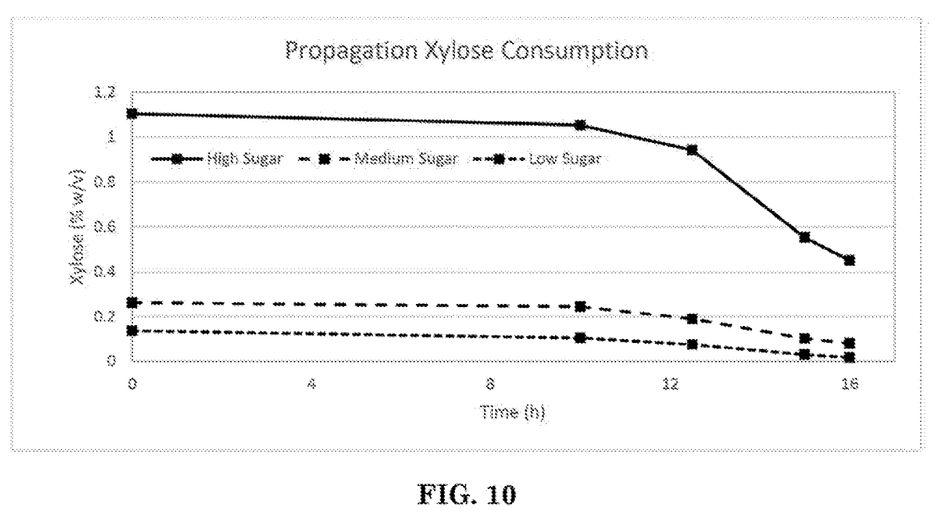
FIG. 10 is a graphical representation of xylose consumption during propagation according to an embodiment.

High performance liquid chromatography was used to test for sugar and ethanol concentrations during both propagation and fermentation and as shown in FIGS. 3, 4, and 6-8. Propagation samples were also plated using yeast extract, peptone, xylose, and penicillin agar plates to determine propagation and as shown in FIG. 5.

The results show that the yeast was propagated on the compositions containing inhibitors and no added sugars. The resultant propagated yeast was able to ferment the sugars to produce ethanol.

Example 2 (Different Sugar Levels with Furfural Stripping)

A slurry obtained from a commercial lignocellulosic ethanol facility containing acid pretreated and enzymatically hydrolyzed corn stover was used for propagation. The acid pretreated and enzymatically hydrolyzed corn stover was first air stripped to remove furfural and then combined at different levels with grain ethanol thin stillage and variable water to create different propagation slurries referred to as High Sugar, Medium Sugar, and Low Sugar.

The High Sugar propagation slurry contained about 93 ppm furfural, 73 ppm HMF, 0.18% w/v acetic acid, 1.65% w/v glucose, and 1.10% w/v xylose.

The Medium Sugar propagation slurry contained about 27 ppm furfural, 19 ppm HMF, 0.06% w/v acetic acid, 0.41% w/v glucose, and 0.26% w/v xylose.

The Low Sugar propagation slurry contained about 15 ppm furfural, 11 ppm HMF, 0.04 weight percent (w/v) acetic acid, 0.24% w/v glucose, and 0.14% w/v xylose.

The propagation slurries were each added to 70% volume of the 6.6 L Bioflo 310 bioreactor. The bioreactors were aerated and controlled at 31.1° C. and pH 5.5. The commercially available antibiotic Lactoside 247 was added at 13 ppm. Active dry yeast from Novozymes was added at approximately 0.05 g/L DCW. The propagation was allowed to continue until dissolved oxygen and NIR testing showed that sufficient sugar had been consumed by the yeast (>50% xylose or glucose consumption). Once propagation was complete, 10% by volume propagation slurry was combined with 90% by volume of acid pretreated and enzymatically hydrolyzed corn stover previously pH adjusted to 5.5 in a shake flask topped with a water lock. The various fermentation compositions were allowed to ferment for 72 hour at 32° C. in an air shaker incubator.

Each fermentation composition contained 2183 ppm furfural, 143 ppm HMF, 0.29% w/v acetic acid, 3.1% w/v glucose, and 2.2% w/v xylose.

Figure 11:
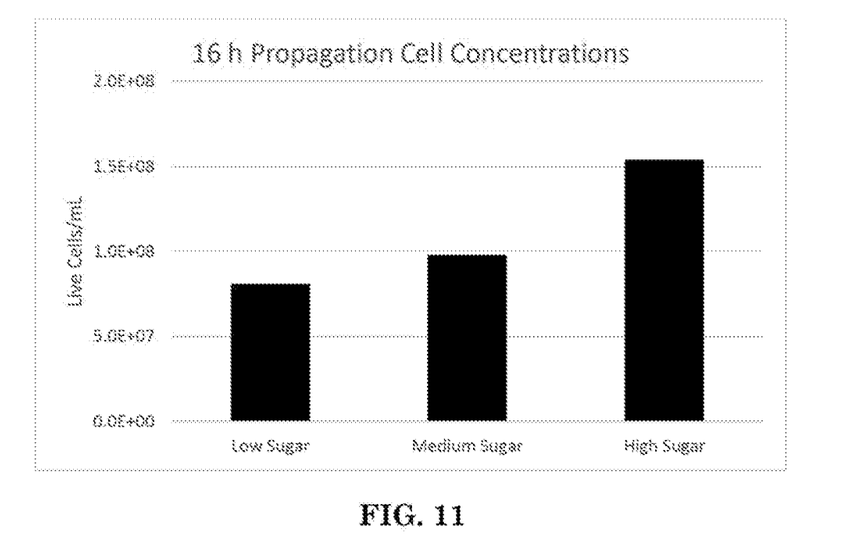
FIG. 11 is a graphical representation of propagation as determined by a live cell concentration according to an embodiment.
Figure 12:
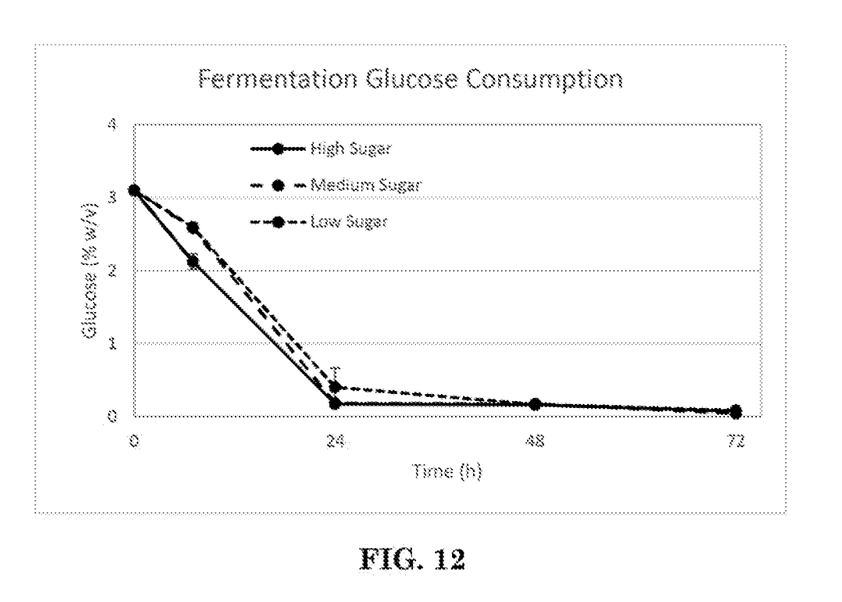
FIG. 12 is a graphical representation of glucose consumption during fermentation according to an embodiment.
Figure 13:
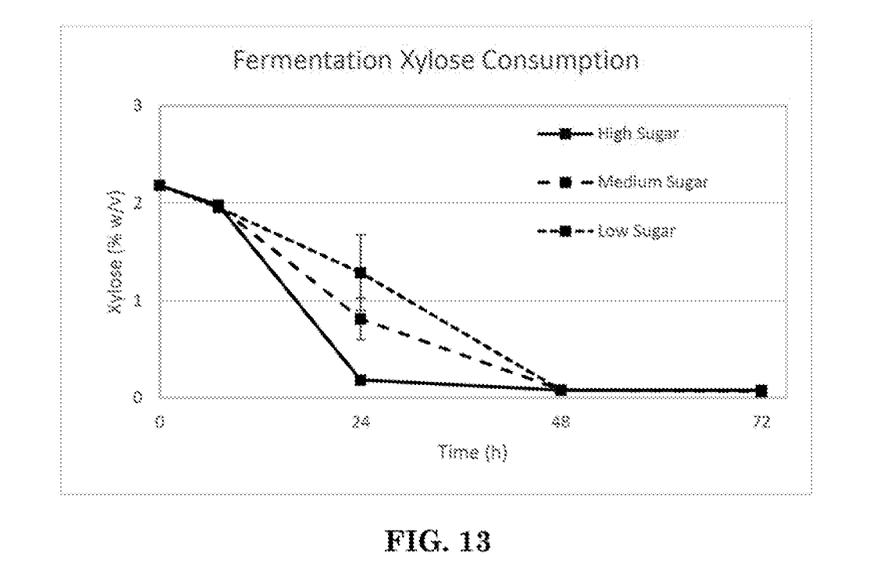
FIG. 13 is a graphical representation of xylose consumption during fermentation according to an embodiment.
Figure 14:
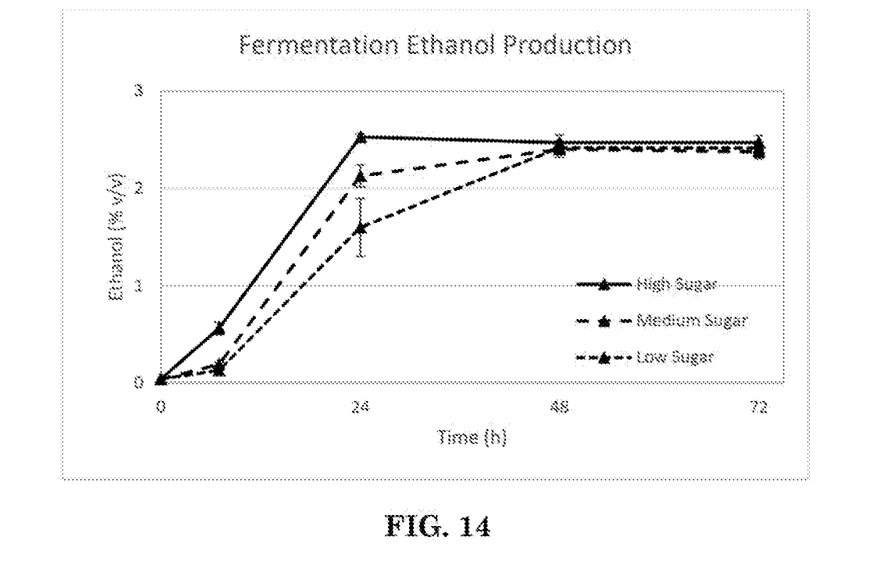
FIG. 14 is a graphical representation of ethanol production during fermentation according to an embodiment.

High performance liquid chromatography was used to test for sugar and ethanol concentrations during both propagation and fermentation as shown in FIGS. 9, 10, 12-14. Propagation samples were also tested using a Nexcellom Cellometer to determine a live cell concentration and as shown in FIG. 11.

The results show that yeast propagated on higher sugar amounts resulted in higher cell concentrations and better fermentation rates.

What is claimed is:

1. A method of propagating a microorganism, the method comprising:
   a) providing a propagation medium comprising at least a lignocellulosic hydrolysate comprising at least one monosaccharide, the at least one monosaccharide at a concentration from about 0.1 wt % to 2.0 wt % of the propagation medium, and at least one inhibitor at a concentration of about 200 ppm or less, wherein the at least one inhibitor comprises furfural;
      wherein the lignocellulosic hydrolysate is formed by:
      (i) providing lignocellulosic biomass comprising hemicellulose, cellulose, and lignin;
      (ii) hydrolyzing at least a portion of the lignocellulosic biomass into one or more oligosaccharides or one or more pentoses, hexoses or both to form a first hydrolysate composition comprising at least pentose, cellulose, lignin, and inhibitors comprising furfural;
      iii) enzymatically hydrolyzing at least a portion of the cellulose in the first hydrolysate composition to form a second hydrolysate composition comprising at least pentose, hexose, lignin, and inhibitors comprising furfural; and
      iv) reducing a concentration of at least the furfural in the second hydrolysate composition to form the lignocellulosic hydrolysate;
   b) growing a first cell mass of the microorganism on the propagation medium to form a second cell mass of the microorganism, wherein the second cell mass of microorganism is greater than the first cell mass of the microorganism;
   c) adding additional lignocellulosic hydrolysate composition to the propagation medium and growing the second cell mass of microorganism to form a third cell mass of the microorganism, wherein the additional lignocellulosic hydrolysate composition has a furfural concentration greater than 1000 ppm; and
   d) after "c", providing cell mass from the third cell mass of the microorganism to fermentation to produce a fermentation product.

2. The method as in claim 1, wherein the first cell mass of the microorganism is from about 0.001 wt % to 0.05 wt % of propagation medium.

3. The method as in claim 1, wherein the at least one inhibitor further comprises 5-hydroxymethylfurfural (HMF).

4. The method as in claim 1, wherein the concentration of furfural in the second hydrolysate composition is greater than 1000 ppm.

5. The method as in claim 1, wherein the reducing is by dilution or gas stripping or both.

6. The method as in claim 5, wherein the gas stripping is performed with air, nitrogen, ozone or combinations thereof.

7. The method as in claim 1, wherein the second cell mass of the microorganism comprises 100 to 1000 times the first cell mass of microorganisms.

8. The method as in claim 1, wherein the propagation medium further comprises a stillage component, the stillage component is selected from whole stillage, thin stillage, wet cake, syrup, and combinations thereof.

9. The method as in claim 8, wherein the stillage component is thin stillage.

10. The method of claim 1, wherein substantially no ethanol is produced by the first cell mass of the microorganism or second cell mass of the microorganism during the growing time period.

11. The method of claim 1, wherein the growing the first cell mass of the microorganism when combined with the propagation medium is at about 20° C. to 37° C. at pH from about 4 to 6 within a time period from 12 hours to 48 hours such that the second cell mass of the microorganism is present in an amount in the range of from 10 times to 30 times the first cell mass.

12. The method as in claim 11, wherein after adding additional lignocellulosic hydrolysate composition the propagation medium has a monosaccharide concentration greater than in step "a)".

13. The method as in claim 1, wherein the fermentation product is ethanol.

14. The method as in claim 1, wherein the microorganism comprises yeast.

15. The method as in claim 14, wherein the yeast is *Saccharomyces cerevisiae*.

16. The method as in claim 1, wherein the microorganism is capable of growing on glucose, xylose, arabinose or a combination thereof.

17. The method of claim 1, wherein the hydrolyzing at least a portion of the lignocellulosic biomass is by acid hydrolysis to form an acid-treated hydrolysate and optionally subjecting the acid-treated hydrolysate to steam explosion to form the first hydrolysate.

18. The method of claim 1, wherein the additional lignocellulosic hydrolysate composition comprises at least a portion of the first hydrolysate composition and/or at least a portion of the second hydrolysate composition.

* * * * *